United States Patent [19]

Cherubini

[11] Patent Number: 5,316,545
[45] Date of Patent: May 31, 1994

[54] POLYMERIC ORTHOTIC DEVICES AND METHOD OF FORMATION

[75] Inventor: Julian H. Cherubini, Newton, Mass.

[73] Assignees: Nicole A.; Alexandra Cherubini, Newton, Mass.

[21] Appl. No.: 982,877

[22] Filed: Nov. 30, 1992

Related U.S. Application Data

[63] Continuation of Ser. No. 755,833, Sep. 6, 1991, abandoned.

[51] Int. Cl.5 .............................................. A61F 5/00
[52] U.S. Cl. ........................................... 602/7; 602/6; 602/900; 264/222
[58] Field of Search .............. 602/6, 7, 8, 10, 48, 602/900; 36/154, 173, DIG. 2; 264/222, 230, 342

[56] References Cited

U.S. PATENT DOCUMENTS 3,692,023  9/1972  Phillips et al. ..................... 602/7
4,704,129 11/1987  Massey ............................. 264/222

Primary Examiner—Richard J. Apley
Assistant Examiner—Lynne A. Reichard
Attorney, Agent, or Firm—Wolf, Greenfield & Sacks

[57] ABSTRACT

A preform for use in forming orthotic devices which have a memory in the original preform shape. The preform is preferably formed into a final body shape which retains a memory of the original preform shape.

6 Claims, 1 Drawing Sheet

POLYMERIC ORTHOTIC DEVICES AND METHOD OF FORMATION

This application is a continuation of application Ser. No. 07/755,833 filed on Sep. 6, 1991, now abandoned.

FIELD OF THE INVENTION

The field of this invention is the orthopedic field and the provision of orthotic devices such as heel, ankle and hand supports as well as methods of manufacture of such devices.

BACKGROUND OF THE INVENTION

A wide variety of orthotic devices are known for use in correcting body problems or supporting body structures such as broken or displaced bones, strained or stretched tendons and ligaments or post-surgical repair.

Most orthotic devices which are custom made of thermoplastic polymeric materials use flat sheets as starting materials. The flat sheets are heated and softened, draped over molds cooled and hardened, thus forming a finished part. The molds used are generally made from plaster and this requires the taking of plaster impressions from the body part such as an arm or foot region with later formation of a positive mold made from the plaster negative mold.

In some cases, the draping process can be assisted by vacuum forming, pressure forming or other common molding techniques. These products, whether or not formed directly around the body, have a disadvantage in that they produce oversized parts which must be cut to size and then finished, usually in hand operations. The cutting and finishing times can be lengthy and time-consuming.

Conventional plastics used where molds are draped, generally have too high a temperature when moldable to be applied directly to the body and formed.

More recently, in another method of making orthotic devices, low temperature polymeric materials or plastics are used. These plastic materials become malleable at a relatively low temperature as, for example, between 150°-160° F. and can be applied directly to the body so as to obtain the correct body shape while molding. In some cases, flat sheets of such low temperature plastic materials can be pre-cut to the amount of preliminary preparation and to reduce the amount of secondary finishing.

When complex shapes are made or the amount of forming is large, there is some difficulty. In some cases, the low temperature plastics tend to be thinned in critical areas and in an uncontrolled way. This can weaken and reduce the rigidity of the orthosis in an undesirable way.

Plastics formed by conventional techniques from sheet material also have the tendency to revert to their original shape as, for example, the flat sheet from which they are made. Sometimes a formed orthotic must be reheated and modified. Reversion to the original flat sheet often prohibits such a modification, especially if the original orthotic was trimmed. Such reversion is generally due to the processing characteristics of the plastic. For example, in sheet formation, some stretching and orientation may occur in manufacture and in some cases, if the sheet is anisotropic and subsequently cross-linked, there is a tendency to bring the material back to sheet form under certain conditions of use. Such conditions of use are usually those conditions that exceed normal general use but are present on extremely hot days. Also, should a complete, shaped orthotic be reheated for subsequent modification, it returns to its original flat shape.

SUMMARY OF THE INVENTION

It is an object of this invention to provide a preformed orthotic device which can be shaped to conform to a body configuration and which is provided with a memory so as to maintain that body configuration throughout a variety of conditions of use and which can be re-formed to a variety of variations on the original shape.

Another object of this invention is to provide a means and method in accordance with the preceding objects which can be easily formed from a variety of preforms into a final configuration with minimized cost, finishing requirements, and complexity, yet having a structurally strong and desirable body conformance.

According to the invention, a polymeric orthotic device preform has a memory. The device has a first orthotic shape which is defined by the memory. If the device is heated to a point where the plastic is soft and moldable, it will tend to remain in the orthotic shape. The shape will change only by the application of an external force. The polymeric orthotic device preform is capable of being stretched and molded into a second orthotic device shape of larger dimension than the first orthotic shape but generally conforming to the overall configuration to the first orthotic shape. Thus, an orthotic device can be stretched and formed over the body of a user. Such a formed device can be essentially stable in shape but when subject to extreme conditions of use, will resist being distorted from its conforming shape to the body of the user because of the memory of the device. In a single step by the practitioner, an orthoic device can be custom fitted and biomechanical corrections imparted to it without the need of secondary finishing.

In a preferred embodiment, the polymeric material is a caprolactone polymer which has a molecular weight of about 50,000 and a melting point of about 58°-60° C. with a specific gravity at 20° C. of 1.10 at melt and a viscosity of 1.5 million centerpoise at 100° C.

According to the method of this invention, an orthotic device can be formed by selecting a polymeric material preform comprising a plastic material and having a first orthotic shape and a memory imparted to said preform. The preform is selected to be close in size but smaller than a body area to be covered and is generally of a configuration similar to said body area.

The preform is then molded against the body to conform to the body area under conditions such as heating and softening, which retain the memory of the first shape and require some stretching of the material to conform to the body area shape. As the material cools, it reverts to its original mechanical properties and still retains the memory of the preform, but it holds the shape that it is molded to, so as to conform to the body area.

In a preferred embodiment, the orthotic device is a heel cup and ankle support. Such heel cup and ankle supports can be made in three or four standard overall adult sizes and can be of caprolactone polymer. The polymer can be molded to the preformed sizes and then cross-linked to give it a memory such that when heated to soften it from the original shape, it may be stretched from said preformed shape around the body part or mold. If reheated, it will tend to return to said preformed shape at certain conditions of use such as reheating.

It is a feature of this invention that the plastic memory imparted to the preform is such that under normal conditions of use, the memory will be unnecessary since the preform when molded to the shape of the body, will maintain that molded shape. However, under extreme conditions of use such as at highly elevated ambient temperatures which may occur at times with or without high pressure as in the heel cup use, any change in the shape will be a change tending to return the heel cup to its original smaller shape and thus, tighten and enhance the stability and conformance of the device.

BRIEF DESCRIPTION OF THE DRAWINGS

The above and other objects, features and advantages of the present invention will be better understood from the following specification when read in conjunction with the accompanying drawings in which.

BRIEF DESCRIPTION OF PREFERRED EMBODIMENTS

Figure 3:
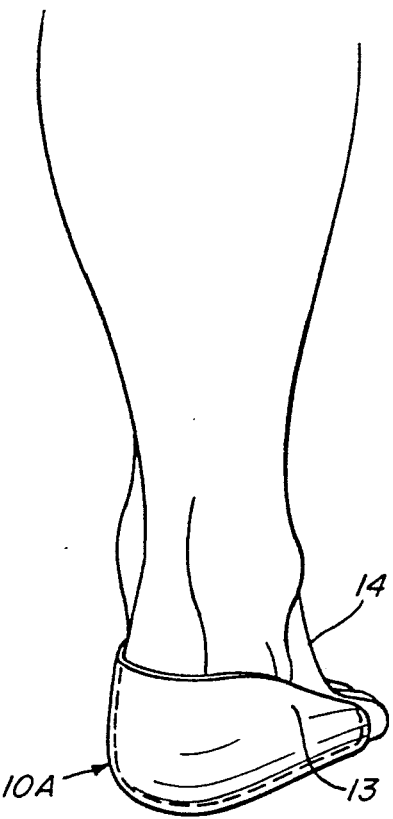
FIG. 3 is a side view of the preform after molding into a second shape conforming to the heel and ankle area of a user's foot on the body with which the orthotic device is used.

According to the invention, an orthotic device preform 10 is first formed of a plastic or polymeric material which has or can be processed to have a plastic memory. The preform is illustrated in side view at 10 in the form of a heel cup and ankle support. The heel cup 10 has an upstanding side wall 11 and a bottom 12. The preform 10 is formed into its final shape by molding to a final body configuration of a heel cup, as shown in FIG. 3 at 10A on the foot 14 of a user.

While the preformed orthotic device of this invention is illustrated in this application as a heel cup and ankle support, the preform can be of various shapes and configurations to act as an orthotic device for many uses. For example, the orthotic device preform can be one designed for use with elbows, wrists, knees, ankles or other shapes.

In all cases, the preform is a form closely conforming to the final shape of the orthotic device to be made and of smaller overall therapeutic dimensions than the final device or second shape to be formed from the preform. By therapeutic dimensions, it is meant that where a certain amount of pressure is to be applied to the ankle support or the like, one wants to select a preform that will apply that pressure at the desired area as it may return to its preform shape even though stretched to a second shape during a molding operation. Thus, the device does not loosen but rather will tend to hug and more closely grip the exact contours of the body when it is soft and being molded to the body. An analogy here is a latex rubber glove which is smaller than the hand, but when put on, stretches to fit the exact body. Unlike the glove, our preform will not exert a compressive elastic force when it cools and hardens and will retain the limb configuration if removed from the limb.

The materials useful for the preforms of this invention are any materials which can be provided with a memory in their preform shape. The word "memory" as used in this application is meant to describe the characteristic of memory of plastics or polymeric materials to return to an original shape after distortion from the original state such as molding to a second shape if certain conditions are met, which conditions are usually conditions of a second heating to a heat lower than the melting temperature of the plastic yet high enough to cause deformation of the plastic towards its preform shape. The temperature necessary to activate the memory is generally the same as the second shape molding temperature. The preformed shapes can be imparted memory by various means depending upon the particular plastic or polymeric material used. For example, the memory to return to an original or first shape can be set into that first shape by mechanical forming, chemical radiation or other cross-linking, predetermined stretching, molding in place or other known procedures. In all cases, it is important that when the polymeric material is stretched to a second shape, it has a memory to return to its first shape under extreme conditions of use. For example, when a plastic material is formed as a preform and then stretched to exactly meet the contours of the body in a particular application, it will stay in that second shape under ordinary ambient conditions. However, if reheated to modify or change it, the material will tend to shrink back towards and approach its original configuration. Usually this is a temperature related phenomenon.

Preferred plastic materials which are capable of having a memory imparted to them include, but are not limited to, caprolactone polymer sometimes known as oxepanone polymer which can be a polymer having the formula

H[O(CH2)5CO]x O(CH2)4-H[O(CH2)5CO]yO and can contain caprolactone polymer initiated with butane diol. Such polymers are known in the art and are sold under the trade name "Capa 650" by Acquaplast Corporation of Wyckoff, N.J. Such polymers can have molecular weights of about 50,000, melting points of 58°-60° C. with a freezing point of approximately 35° C., flashpoint of 250° C. open cup, specific gravity at 20° C. of 1.10 at melt and viscosity of 1.5 million centerpoise at 100° C.

Other polymers known in the orthopedic art and other substitutes therefor which are useful for forming mold-in-place orthopedic and orthotic devices can be used as, for example, noted in U.S. Pat. No. 4,019,505. This patent notes the use of a thermoplastic polyester having a melting point between 40° C. and 70° C. which is a poly(epsilon caprolactone) polymer having an average molecular weight of over 30,000. Such materials soften at a sufficiently low temperature that they can be formed directly on a patient without undue injury due to scalding or burning. There are quite a few such high polymers which melt or soften at temperatures ranging from 40° C. to 70° C. which can be used for forming orthotics without causing skin damage. In some cases, higher temperatures can be used when the orthotic is to be formed over a protective layer, although it is preferred that the orthotics of this invention are formed directly on the skin from a preform into a second shape. However, the orthotic can be formed over a secondary mold which may be identical to the body or in a desired configuration for use on a specific body part. The orthotic thus can be formed over a body mold which can be the body itself or a mold designed to give a body fit to the orthotic.

Among the materials which melt in the most desired range are poly(ethylene adipate), poly(epsilon caprolactone), polyvinyl stearate cellulose acetate butyrate, and ethyl cellulose. The first three materials mentioned exhibit true crystalline melting in this temperature range. In the case of cellulose acetate butyrate and ethyl cellulose the phenomenon noted is the so-called glass transition temperature. Poly(propylene oxide) has a crystalline melting temperature of 74° C. This temperature is a little high to be considered for this use, but as is well-known in the art, judicious addition of comonomers to the poly(propylene oxide) will yield a lower melting temperature.

Such materials preferably have high stiffness so that they can be used at thickness ranges of, preferably, from 1/32" to ¼" and provide considerable support to the body with which the orthotic device is used. Thickness up to ½" or higher can be used in some cases. For example, a 1% secant modulus of 50,000 psi at 23° C. is useful. Other known materials of this type can be used in the present invention.

In the preferred embodiment of this invention, where caprolactone polymer materials are used, preform wall thicknesses of from 1/64" to ¼" inch are preferred for normal orthotic purposes. For example, in the case of heel cups, the walls thickness of the preform and resulting second shape orthotic device is preferably in the range of the 1/16" to 3/16" and in the preferred embodiment is about ⅛". The wall thickness can vary in both the preform and final product by small amounts as, for example, by shaping of the preform to form the second shape and final orthotic product. In all cases, the wall thickness and material used is sufficient to provide the .orthotic support or correction required with the particular device used.

Figure 1:
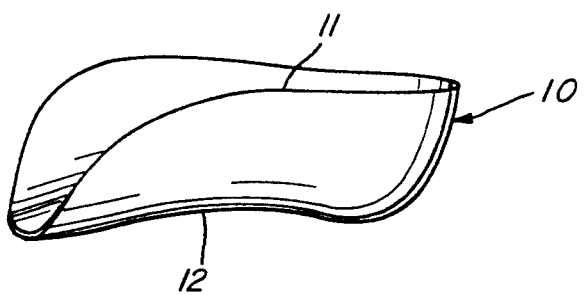
FIG. 1 is a side view of a heel cup and ankle support orthotic device in accordance with the present invention (preform)
Figure 2:
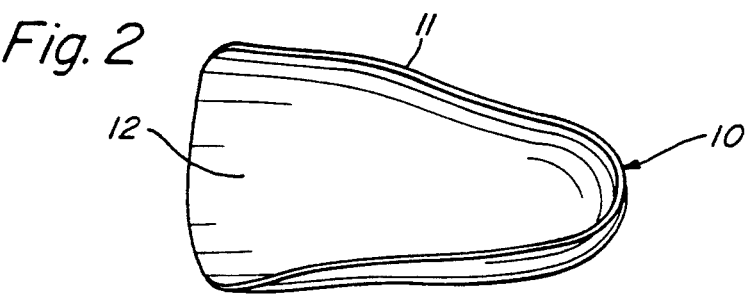
FIG. 2 is a top plan view thereof.

In normal use, the preform 10 can be formed by any of a number of ways, but preferably is formed by molding to roughly conform to the shape of a body to which it is used. In the case of heel cups, there may be three or more preform sizes used to cover substantially all adult foot sizes with which the orthotic might be used. In an example of FIG. 1, a small size heel cup is formed of caprolactone polymer having a thickness of ⅛", a front-to-back length of 4", a side to side outside dimension of 2" at its widest point and a wall height as shown in FIG. 1 of 1½".

The device 10 is made in a simple compression mold consisting of a male and female mold block. Injection molding, vacuum forming, pressure molding, compression molding and other means can be used to make the preform 10 which is to have a memory. In some cases, the preform 10 can be made with a plastic memory of the shape in which it is in although in most cases, the preform will not have a memory at its first stage of treatment. In a second step, the caprolactone preform 10 is cross-linked by radiation so as to impart to it a memory which will cause the material to return to the shape as shown in FIG. 1 when temperatures of 140° F. to 200° F. are reached.

In a third step after the cross linking step, the orthotic device is formed into its second and final shape by stretching the heel cup 10 over the foot of a user to deform the material and stretch it at a temperature of from 140° to 200° F. from its original dimensions by perhaps as little as ⅛-inch. Preferably, the degree of stretch is approximately from 1/16 to ½ inch over the field of use. This degree of stretch is kept low by selecting a preform which is slightly smaller in all or part than the body part to which it is to conform in its second shape.

In the case of the device preform 10, it is fit over a slightly larger heel area of the body stretched to fit at a soften temperature of, for example, 140° to 200° F. This final formation in the second shape can be done by a practitioner such as an orthopedic trained person as by having the heel cup formed over the foot 12 to stretch it to the foot shape while heated to a temperature in the range of 140° to 200° F.

In ordinary use at ambient temperature, the heel cup remains stiff and substantially unyielding. However, when temperatures exceed 140° F., the heel cup will tend to return to its unstretched form 10, thus conforming more tightly but in an elastic way, to the heel with which it is used. If it is desired to adjust the heel cup after use on the body, this can easily be done by again stretching after softening to a temperature below a temperature which would cause loss of memory. Since the memory is in the preform, as well as the completed original heel cup, the heel cup can be reformed and adjusted in whole or in part as desired. In some uses, the ability to reform as the body heals, and changes in shape are needed, is a significant advantage.

Note that FIG. 3 shows the heel cup 10A conformed to the foot of a user with the ankle support portion 13 shown slightly deformed to an orthotic shape. The second shape of the heel cup in the form 10A is slightly larger then the original shape of the heel cup 10 and has a memory imparted by having cross linked the preform to bring it back to its smaller dimensions under predetermined conditions such as after stretching if it is reheated.

Note that because the preform is slightly smaller than the heel cup and because the body is merely pressed against the heel cup to deform it to the shape 10A, the practitioner forming the orthotic need not be as highly skilled as one who would form an original shape from a flat sheet or from molded items. The need for specific foot molds is eliminated. The heel cup 10A can be re-used and reformed on another foot if desired. There is a timesavings for the practitioner in that a simple series of steps can be used to form a final orthotic product.

No material pre-cutting, pasting, special fit or plastic finishing is necessary in the orthotic devices formed by the present invention.

Positional control of various bones or other body elements can be easily accomplished by conforming the preform to a specific area of the body as the preform stretches or other shape changes with heating so as to automatically obtain desired shapes and supports. For example, if a pressure relief area is desirable, the foot may be spot padded so that subsequent orthotic is formed over the foot and pad.

In all cases, the orthotic second shape is formed by a structurally strong supporting orthotic which provides the desired support to the device.

In all cases, a plastic memory is useful to assure that if there is a change in configuration from the second shape of the orthotic device, that change will be a tightening change to make the device even more closely conform to the body of the user.

What is claimed is:

1. A method of forming an orthotic device comprising, selecting a polymeric material preform having a first, non-planar orthotic shape and having a memory imparted to said preform, said preform being selected to be molded over a predetermined body area of larger configuration than said first orthotic shape, molding said preform to conform to said body area under conditions which retain said memory, wherein said preform being formed by a molding step and processed to provide a memory in said preform in a first shape when said orthotic device is stretched form said first shape, and stretching said preform from said first shape to mold said preform to said body.

2. A method in accordance with claim 1, wherein said molding is carried out by stretching and heating below a temperature which would cause loss of said memory.

3. A method in accordance with claim 2, wherein said preform is crosslinked to impart memory prior to said molding step.

4. A product according to the method of claim 3.

5. A method in accordance with the method of claim 1, wherein said processing is carried out by cross-linking of the polymeric material of said preform.

6. A product according to the method of claim 1.

* * * * *